United States Patent [19]

Mayeur

[11] Patent Number: 5,384,535
[45] Date of Patent: Jan. 24, 1995

[54] ELECTRIC MAGNETIC DETECTOR OF MAGNETIC PARTICLES IN A STREAM OF FLUID

[75] Inventor: Jean-Pierre Mayeur, Villepreux, France

[73] Assignee: Le Bozec Aeronautique, Nanterre, France

[21] Appl. No.: 9,142

[22] Filed: Jan. 26, 1993

[30] Foreign Application Priority Data

Jan. 27, 1992 [FR] France .................. 92 00812

[51] Int. Cl.⁶ ............... G01N 27/74; G01N 15/06; G01N 27/02; F16N 29/04
[52] U.S. Cl. .................. 324/204; 324/693; 340/631
[58] Field of Search .......... 324/204, 228, 693; 340/627, 631

[56] References Cited

U.S. PATENT DOCUMENTS

| 3,432,750 | 3/1969 | Botstiber | 324/204 X |
| 4,008,464 | 2/1977 | Hobbie | |
| 4,766,373 | 8/1988 | Chambers et al. | 324/204 |
| 5,179,346 | 1/1993 | McGee et al. | 324/204 X |

FOREIGN PATENT DOCUMENTS

| 0290397 | 11/1988 | European Pat. Off. |
| 2564897 | 11/1985 | France |
| 2641087 | 6/1990 | France |
| 2029580 | 3/1980 | United Kingdom |
| 2042182 | 9/1980 | United Kingdom |
| 2219405 | 12/1989 | United Kingdom |

Primary Examiner—Gerard R. Strecker
Attorney, Agent, or Firm—Young & Thompson

[57] ABSTRACT

An electrical magnetic detector disposed in the passage of a flow of fluid to detect the magnetic particles transported by that flow and to trigger an alarm after detection of a predetermined quantity of magnetic particles. It includes a magnet surrounded by two polar masses separated by an axial air gap. The external surface of the detector has, at least adjacent the air gap (4), peripheral surfaces (5, 6) converging toward the air gap. The detector is useful in the surveillance of wear members to detect the degree of wear thereof.

6 Claims, 2 Drawing Sheets

ELECTRIC MAGNETIC DETECTOR OF MAGNETIC PARTICLES IN A STREAM OF FLUID

FIELD OF THE INVENTION

The invention relates to a magnetic detector of the type adapted to be disposed in the passage for a flow of fluid to detect the metallic particles transported in said flow and to trigger an alarm after detecting a predetermined quantity of metallic particles, of the type comprising a magnet surrounded by two polar masses separated by an axial air gap.

BACKGROUND OF THE INVENTION

Such detectors are used in particular for detecting the deterioration of wear members, for example motors such as reactors, and/or instances of malfunction, producing the separation of metallic particles which are entrained in a flow of fluid such as a flow of oil or of refrigerant. These metallic particles are to be detected by the magnet of the detector, which can trigger an alarm for a predetermined quantity of particles. The detected particles are magnetizable particles, either because they derive from a metallic member, or because they originate from a non-magnetic material but which is secured to a magnetic material. The detection of the particles permits the preventive maintenance of the mechanical members by continuous control of their deterioration.

For high efficiency, such detectors must attract a very high proportion of the particles passing in their vicinity, even though the fluid flow is at high speed and when said fluid has a tendency to retain the particles, for example in the case of a viscous fluid such as an oil.

Moreover, the detected particles should be concentrated in the air gap to produce if desired an alarm, the filling up of the air gap closing an electrical alarm circuit.

Of course, these phenomena of detection differ according to the nature of the particles, their sizes, the nature of the carrier fluid and its speed of flow.

The known detectors of the type indicated in the introduction are constituted by a magnet surrounded at each of its two ends by a polar mass.

The magnet is a known Al-Ni-Co alloy.

The users of these known detectors have noted numerous drawbacks and deficiencies. In particular, the efficiency of detection of the particles, which is to say the ratio of the number of particles detected to the number of particles injected in the course of a trial (in %) is low, even for large particles (1000 $\mu$m).

Moreover, the magnets used are subject to accelerated aging because of the high temperatures (of the order of 175° C. for example for a motor oil), the aging being moreover permanent. Moreover, these magnets can be remotely demagnetized, for example to permit the use of a magnet to collect the detected particles.

Moreover, in the case of the use of the detector for triggering an alarm by closure of an electric circuit by the detected particles covering the air gap, it has been determined that the particles do not have the tendency to accumulate in the air gap, such that a very high total number of detected particles is necessary to trigger the alarm.

SUMMARY OF THE INVENTION

The present invention aims to overcome these drawbacks of the known magnetic detectors.

To this end, the detector according to the invention is characterized in that its external surface has, at least adjacent the air gap, a peripheral surface converging toward said air gap. Tests that have been conducted have shown that such a converging shape increases the gradient of the magnetic field about the air gap, which increases the efficiency of detection and promotes the retention of the detected particles. Moreover, in the case of an electrical detector, this shape promotes the accumulation of the particles in the air gap or at least in its vicinity.

According to a first embodiment, the polar masses are of a weakly magnetic material and comprise said external converging surfaces of the detector.

According to a modification, the polar masses are of a magnetic material and are each clad in a spacer of weakly magnetic material comprising respectively said external converging surface of the detector.

According to another embodiment, the detector comprises two magnets mounted in opposition and separated by a magnetic mass, the opposite ends of each of the magnets being provided with a polar mass of magnetic material, a spacer of weakly magnetic material comprising said external surface surrounding each of said magnets and the associated polar mass.

These three embodiments of the invention permit, at increasing cost, detection efficiencies which also increase, such that they are each used as a function of the desired detection efficiency. In particular in the case of an electrical detector, a too-high detection efficiency could result in triggering alarms untimely or prematurely, such that as a function of the purpose of the detector and a predetermined alarm level, there will be chosen one or the other of the preceding types of detectors, of course adapting the variables such as the air gap, the exact shape of the converging surfaces and the size of the components, particularly of the polar masses.

In particular, in the case of the last modification, the thickness of the magnetic mass separating the two magnets is double that of the polar masses which are of the same thickness as each other. There is thus obtained an optimum concentration of the particles in the medial portion of the air gap.

The detector according to the invention can be used for a visual or electrical control, the detector being associated or not, in known manner, with an auto-closure.

According to a preferred embodiment of the invention, the magnet or magnets are samarium-cobalt magnets. The risk of remote demagnetization is thus avoided and high temperature aging is considerably reduced.

Preferably, the magnet or the magnets and the polar masses are mounted on a hub of non-magnetic material.

BRIEF DESCRIPTION OF THE DRAWINGS

The invention will be well understood from a reading of the following description given with reference to the accompanying drawings, in which.

DETAILED DESCRIPTION OF THE INVENTION

Figure 1:
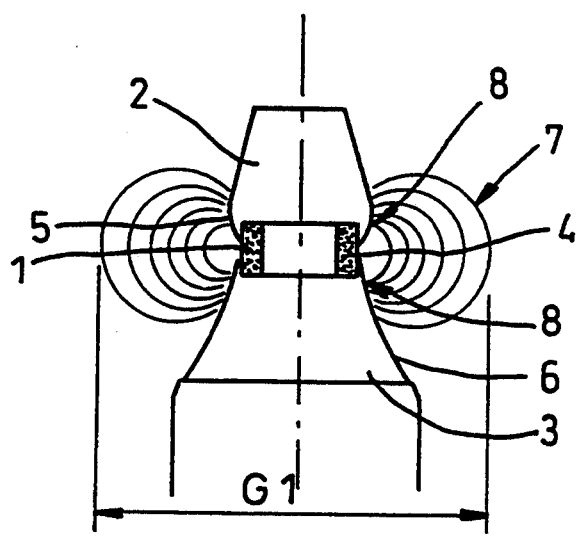
FIG. 1 is a schematic plan view, partly in cross section, of a detector according to a first embodiment of the invention.

The magnetic detector shown schematically in FIG. 1 comprises an annular magnet preferably of samarium-cobalt. The magnet 1 is partially covered by two polar masses 2 and 3 of weakly magnetic material, for example weakly magnetic steel, which are spaced apart on opposite sides of magnet 1 along the axis of magnet 1, leaving between them an air gap 4. The polar masses 2 and 3 have respective external surfaces 5 and 6 adjacent the air gap 4, which converge toward this air gap 4 with, in the illustrated embodiment, a curved cross section.

The assembly creates an induction field 7 of a diameter G1, the displacement or the migration of the detected particles being limited to the lines 8 corresponding to the axial ends of the magnet 1.

Figure 2:
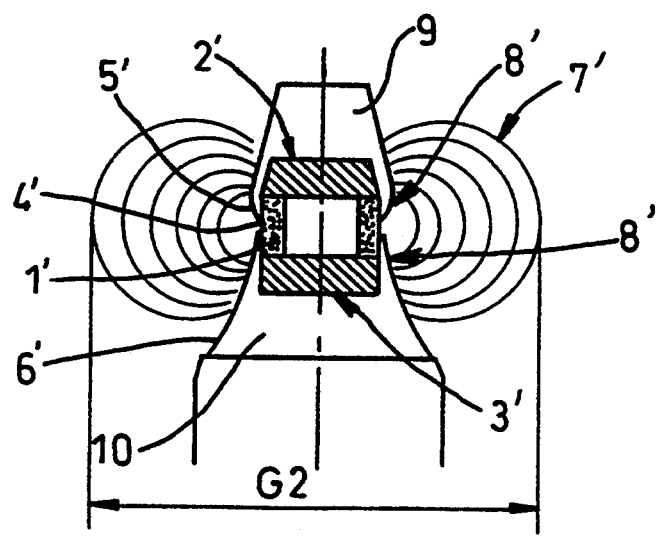
FIG. 2 is similar to FIG. 1, showing another embodiment.

In the embodiment of FIG. 2, the polar masses 2' and 3' are of magnetic material and the assembly is clad in two spacers of weakly magnetic material 9 and 10, respectively, leaving between them the air gap 4' and comprising converging external surfaces 5' and 6'. The induction field 7' has a diameter G2 greater than G1 and the migration of the particles is limited by the lines 8' again determined by the axial ends of the magnet 1'.

Figure 3:
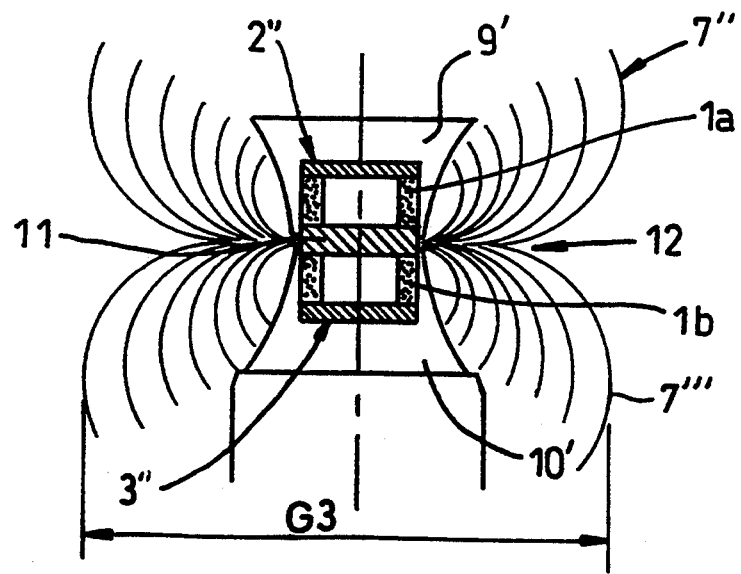
FIG. 3 is analogous to FIGS. 1 and 2, showing a second modification.

In the modification of FIG. 3, the detector comprises two annular magnets 1a and 1b of the same length, which are separated by a ring of magnetic material 11, for example of steel. The polar masses 2" and 3" are of the same magnetic material and have the same thickness as each other, which is half that of the ring 11. The assembly, as in FIG. 2, is partially clad by spacers 9' and 10' of weakly magnetic material, such as weakly magnetic stainless steel, which leave between them an air gap and comprise the external converging surfaces of the detector.

Figure 4:
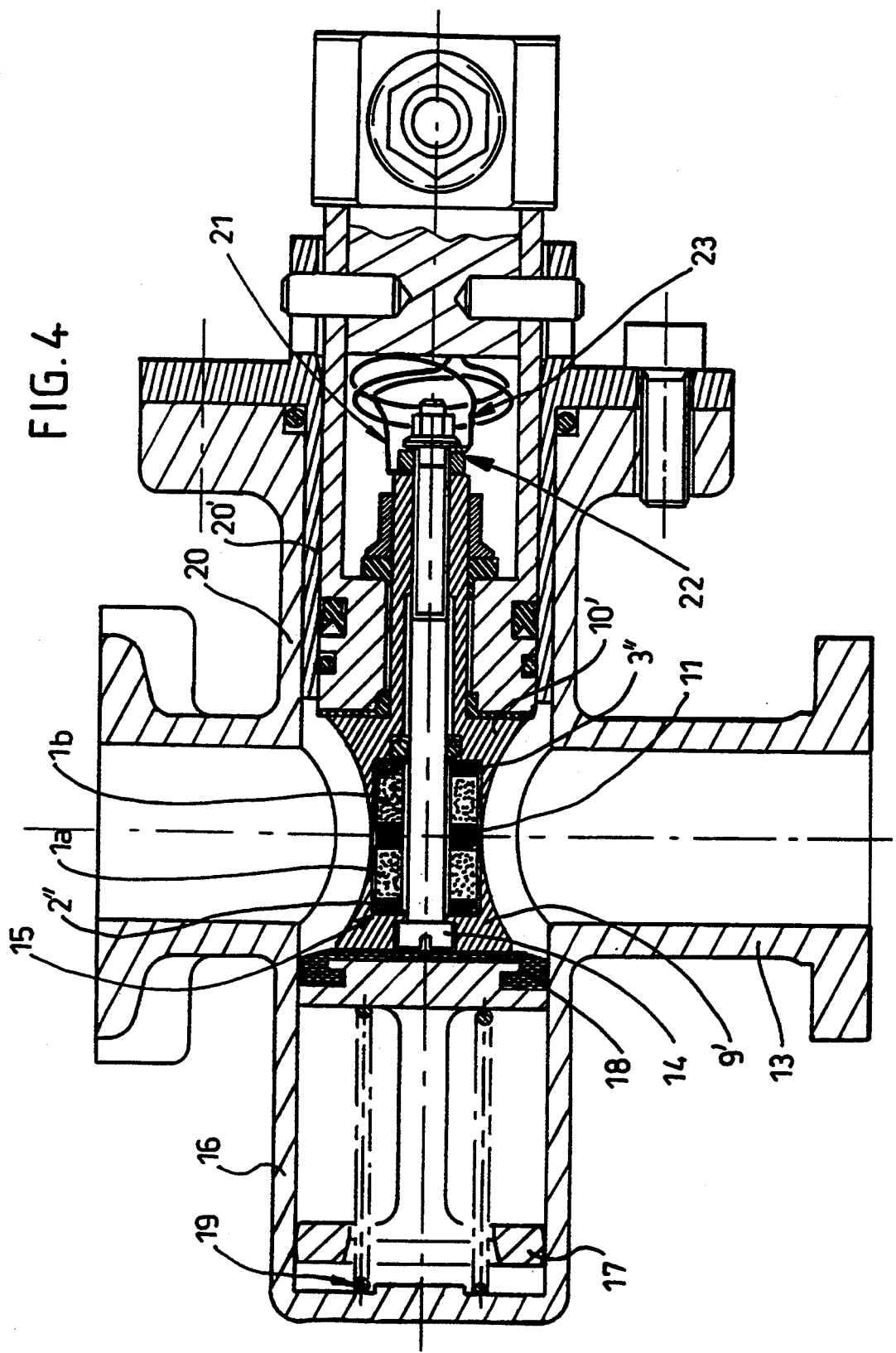
FIG. 4 is a schematic cross-sectional view of a casing adapted to be inserted in a conduit and comprising a detector according to FIG. 3 arranged for electrical detection.

In this arrangement, the induction fields 7" and 7'" have a diameter G3 greater than G2 and G1 and, moreover, the migration of the particles is concentrated in the air gap because the lines 7" and 7'" meet along the plane 12 of the ring 11. This configuration is therefore naturally suitable for the provision of an electrical detector, such as is shown by way of example in FIG. 4.

The detector is disposed in a casing 13 adapted to be inserted in a conduit (not shown) such that the fluid flowing in the conduit passes about the detector. The components of the detector, namely the magnets 1a, 1b, the ring 11, the polar masses 2" and 3" and the spacers 9', 10' are mounted on a hub 14 of amagnetic material ensuring good closure of the fields and are enclosed in an envelope 15 of synthetic material for protection from the environment and for electrical insulation.

The casing 13 comprises a lateral terminal projection 16 in which is disposed a piston 17 bearing on the detector by means of a sealing joint 18 and subjected to the action of a spring 19. The projection 16 is prolonged, on the other side of the casing 13, by a sleeve 20 closed by a closure 20'. This assembly constitutes an auto-closure permitting the removal of the detector without loss of the fluid from the circuit.

The detector is connected to electric terminals 21 and 22 in a detection circuit 23 supplying an alarm or any other conventional indicating or signaling device, the circuit 23 being closed by the particles detected which are in and conductively bridge across the air gap between the adjacent edges of the spacers 9' and 10'.

These edges are not necessarily delimited by flat parallel surfaces. So as to increase the retention of the detected particles, these edges can be given different shapes, for example flat and non-parallel, curved or broken surfaces, etc. . . . creating a trapping effect for the detected particles.

Moreover, one of the spacers 9' and 10' can be slidable on the hub 14 so as to adjust the air gap as a function of the desired level of detection.

Finally, in the case of a non-electric detector, it is possible to arrange between the edges of the spacers an amagnetic ring insulating the spacers from each other and ensuring moreover protection of the magnet or magnets and adapted to provide a collector surface for the detected particles.

I claim:

1. In an electrical magnetic detector adapted to be disposed in a passageway for a fluid to detect the presence of magnetic particles in said fluid, a magnet means comprising a cylindrical member having an axis and two polar masses of weakly magnetic material disposed along said axis surrounding opposite ends of the cylindrical member and spaced apart from each other by an air gap in which migration of said particles is concentrated, said two polar masses having external peripheral surfaces that converge toward each other and toward said axis; the improvement in which said cylindrical member is constituted by two annular magnets of the same length separated by a ring of magnetic material and having on ends of said magnets opposite said ring of magnetic material polar masses of the same magnetic material as said ring and having the same thickness as each other.

2. A detector as claimed in claim 1, wherein said magnets are of samarium-cobalt.

3. A detector as claimed in claim 1, wherein said ring of magnetic material and the last-named polar masses are of steel.

4. A detector as claimed in claim 1, wherein said masses of weakly magnetic material are of stainless steel.

5. A detector as claimed in claim 1, wherein the last-named polar masses each have a thickness half the thickness of said ring of magnetic material.

6. A detector as claimed in claim 1, wherein said ring of magnetic material and the last-named polar masses are of steel, said masses of weakly magnetic material are of stainless steel, and the last-named polar masses each have a thickness half the thickness of said ring of magnetic material.

* * * * *